United States Patent
Yoshitome et al.

(10) Patent No.: US 7,558,681 B2
(45) Date of Patent: Jul. 7, 2009

(54) METHOD OF DETERMINING PLANT SPECIES WITH PYROLYSIS-GAS CHROMATOGRAPHY

(75) Inventors: Shokichi Yoshitome, Miyazaki (JP); Shinichi Tanimura, Miyazaki (JP); Kazuhiro Sata, Miyazaki (JP); Ryo Akashi, Miyazaki (JP)

(73) Assignee: Oki Semiconductor Co., Ltd., Tokyo (JP)

( * ) Notice: Subject to any disclaimer, the term of this patent is extended or adjusted under 35 U.S.C. 154(b) by 467 days.

(21) Appl. No.: 11/253,567

(22) Filed: Oct. 20, 2005

(65) Prior Publication Data

US 2006/0088817 A1    Apr. 27, 2006

(30) Foreign Application Priority Data

Oct. 22, 2004 (JP) .............................. 2004-307989

(51) Int. Cl.
*G06F 7/00* (2006.01)
(52) U.S. Cl. .............................. 702/19; 702/20; 703/11; 707/102
(58) Field of Classification Search ........................ None
See application file for complete search history.

(56) References Cited

U.S. PATENT DOCUMENTS

| | | | | |
|---|---|---|---|---|
| 6,274,319 B1 | * | 8/2001 | Messier et al. | 435/6 |
| 6,441,272 B1 | * | 8/2002 | Ye | 800/278 |
| 6,680,203 B2 | * | 1/2004 | Dasseux et al. | 436/86 |
| 7,135,616 B2 | * | 11/2006 | Heard et al. | 800/278 |
| 2004/0029149 A1 | * | 2/2004 | Palsson et al. | 435/6 |
| 2006/0147899 A1 | * | 7/2006 | Famili et al. | 435/4 |

FOREIGN PATENT DOCUMENTS

JP    2001-95589    4/2001

OTHER PUBLICATIONS

Shachar-Hill (Metabolic Engineering 4:90-97 2002).*
English abstract for JP 2001-95589, 2001.*

* cited by examiner

*Primary Examiner*—Mary K Zeman
(74) *Attorney, Agent, or Firm*—Kubotera & Associates, LLC (57) ABSTRACT

A method of identifying a plant species includes the steps of: preparing a fragment of the plant; heating the fragment to obtain lignin from the fragment; gasifying the lignin at a high temperature to obtain components of the lignin; obtaining a flux profile of the components; and determining the species of the plant.

10 Claims, 13 Drawing Sheets

METHOD OF DETERMINING PLANT SPECIES WITH PYROLYSIS-GAS CHROMATOGRAPHY

BACKGROUND OF THE INVENTION AND RELATED ART STATEMENT

The present invention relates to a method of identifying a plant species, especially rice and lawn glass, with pyrolysis-gas chromatography.

Recently, food safety consciousness, farm product brand certification, and consumer gourmet trend have been spreading, so that a selection criterion for farm products has been focused. Main selection criteria include a production location and a species to be clearly marked on a farm product. For example, identification of rice such as a cultivar, a production location, and a production year are required to be clearly marked on a package material under Japanese Staple Food Control Act. In the near future, such a requirement may be enforced to other farm products of all plants such as lawn glasses and flowers, in addition to rice.

In view of the background, it has been desired to develop new technology for determining a species scientifically, precisely, simply, and rapidly at low cost. In conventional technology, a morphological method, a color of leaf, a grain shape of a fruit tree, and polymorphism of enzyme expression (isozyme pattern) have been used for identifying a species of a farm product or plant. However, it is difficult to analyze cultivar or a similar species. Alternatively, a random amplified polymorphic DNA method (RAPD) has been developed (refer to Japanese Patent Application No. 2001-95589). In the RAPD method, a DNA is extracted from a sample, and the DNA is grown under a suitable random primer with the PCR method. Then, a molecular weight of the DNA is determined with electrophoresis.

In the RAPD method, it is necessary to grow DNA multiple times with the PCR method according to types of primers, thereby making the process complicated, taking long time, and increasing cost. There are many other common bands exist in addition to bands for identification. Accordingly, it is necessary to mix a large number of primers, thereby making it difficult to grow DNA with the PCR method. Among the bands for identification selected from multiple DNA bands, some of them are susceptible to an amplification reaction temperature and a DNA density, thereby causing a repeatability problem.

In view of the problems described above, an object of the present invention is to provide a method of determining a species of a plant rapidly and precisely at low cost without any special morphological method. Especially, when the method of the invention is applied to rice and lawn glass requiring a high quality brand, it is possible to determine a species with simple handling and high reliability at low cost.

Further objects and advantages of the invention will be apparent from the following description of the invention.

SUMMARY OF THE INVENTION

In order to attain the objects described above, according to the present invention, when a test specimen (fragment) is heated, a component is generated from a cell wall by a quantity with the retention time. Then, the component is detected with thermal decomposition gas chromatography or pyrolysis-gas chromatography.

More specifically, according to the present invention, the method of determining a species of a plant includes the steps of: heating a fragment of the plant to extract lignin as a component of a cell wall of the plant, and gasifying the lignin at a high temperature to determine the species of the plant.

According to the present invention, the fragment may be cut from a part of the plant such as a leaf, a stem, and a root.

According to the present invention, the method further comprises the steps of determining a quantity of a component of the lignin, obtaining a flux profile or a time-base spectrum of the component, and determining the species of the plant from the spectrum. The time-base data is detected with pyrolysis-gas chromatography. Further, the method of determining a species of a plant comprises the step of processing the time-base spectrum digitally, and comparing the spectrum with a database to determine the species of the plant.

In the present invention, it is possible to determine a species of a plant sample rapidly and precisely at low cost without any special analytical skill. Especially, when the method of the present invention is applied to rice and lawn glass requiring a high quality brand, it is possible to determine a species with simple handling and high reliability at low cost.

DETAILED DESCRIPTION OF PREFERRED EMBODIMENTS

Hereunder, embodiments of the present invention will be described. A method of determining a species of a plant includes the steps of heating a fragment of a plant sample, extracting lignin as components of a cell wall, gasifying the lignin at a high temperature, detecting the components, and determining the species of the plant.

When a fragment of a plant sample is heated, a weak bond is severed by thermal energy to generate a corresponding decomposed product or component. In the method, it is necessary to suppress secondary decomposition and re-condensation for accurately obtaining a result of a chemical structure of the sample. Accordingly, it is necessary to rapidly heat up to a predetermined temperature to remove the decomposed product from a thermal decomposition apparatus and send the decomposed product to an analyzer connected with the thermal decomposition apparatus.

In the present invention, the components detected with pyrolysis-gas chromatography may be identified through thermal decomposition, gas chromatogram, and mass analyze. The components may include methyl guaiacol, vanillin, isoeugenol, and coniferyle alcohol. According to a known reference, the components are originated from lignin composing a cell wall of a plant.

Lignin is a macromolecular compound having an extremely complicated and irregular structure with phenyl propane as a backbone. It is known that a structure of lignin depends on a species of a plant, whereas details thereof are unknown. When the components of lignin are classified into three main components, i.e., para-hydroxyphenyl, 1-hydroxy-2-methoxyphenyl, and 1-hydroxy-2,6-dimethoxyphenyl, it is possible to determine a conifer, a broadleaf tree, or a grass, however, further determination is difficult.

Lignin is synthesized through secondary metabolism of a plant, mainly via shikimic acid. It is known that lignin thus synthesized has various phenyl compounds as the constituents thereof. Further, it is considered that the secondary metabolism has been modified and changed in the process of evolution of the plant. Accordingly, the constituents of lignin reflect evolution of a species, and a characteristic pattern thereof is different according to the species. The components of lignin are removed from a plant in a specific pattern or a flux profile according to the species of the plant. Accordingly, it is possible to determine the species of the plant through detection of the specific pattern.

The pattern may be detected with, for an example, thermal decomposition (pyrolytic) gas chromatography. When the thermal decomposition gas chromatography is used, it is possible to easily determine a species of a plant without any special analysis or skill for a conventional method.

In the present invention, when a sample is prepared, a heating process, especially a heating temperature, should be carefully determined. As described above, it is necessary to suppress the secondary decomposition and re-bonding of the decomposed products during the heating process. Accordingly, an optimum heating temperature is different according to a species, and generally in the range of 150° C. and 190° C. For example, in case of lawn grass, the heating temperature is set at 170° C.

A cell wall of a plant contains various chemical substances. In the present invention, a particular component among the chemical substances, i.e., lignin, is extracted from a cell wall and detected with thermal decomposition gas chromatography according to the retention time. The present invention may be applied to any known plants having the cell wall. In the invention, dry plant fragments or dry plant ground samples are used for determining a species of a plant. A quantity of a sample is preferably between 10 and 100 mg. A fragment or powder may be obtained from a constituent or a tissue of a plant such as a leaf, a stem, a root, and so forth. As described above, the heating temperature is important to obtain a sample with good quality, and other conditions may be arbitrarily determined.

A method of preparing the sample will be described next. As described above, the basic form of the sample used in the present invention is a dry ground sample or a dry infinitesimal piece of tissue. Accordingly, after collecting a plant, the following processes are performed.

(1) The sample was dried at 60° C. under dry air circulation for 24 hours until moisture content thereof became 10% or less.
(2) The dried sample was cut into fragments having a size of 2 to 3 mm using a severer or a cutter, or was ground to powders using a mill.
(3) The fragments or ground samples were spread to form a thin film having a weight of approximately 0.001 g.
(4) The film sample was thermally decomposed.
(5) Output data was analyzed.

In the present invention, lignin extracted from a cell wall is used for determining a species of a plant. Lignin is the second most abundant organic compound on earth, and forms 25% of constituents of a plant cell wall. As described above, lignin is a macromolecular compound having an extremely complicated and irregular structure with phenyl propane as a backbone thereof. Lignin is produced through a specific metabolic system of a plant, and the chemical diversification thereof is created during evolution of a species. In the present invention, lignin, i.e., a constituent of a plant cell wall, is used for determining a species of the plant through the characteristics particular to each species.

A method of gasifying lignin at a high temperature will be described next. Approximately 0.0014 g of the sample produced by the above processes was analyzed with a curie-point type thermal decomposition apparatus (model GC-17A made by Shimazu Seisakusho) under the following conditions.

Column oven temperature: 50° C.
Sample gasification chamber temperature: 170° C.
Detecting apparatus temperature: 280° C.
Column input pressure: 30 Kpa
Gasification time: 70 minutes A method of determining a species will be described next. Firstly, the measured data is compared with database as follows.

(1) Data obtained by the thermal decomposition is converted to digital data.
(2) A value of the converted digital data is input for search in a database containing specific values particular to species of plants.
(3) A result closest to the value of the converted digital data is output from the database.

A method of creating the database obtained by the thermal decomposition will be described next.

(1) A peripheral PC of the thermal decomposition gas chromatography reads data of an individual plant.
(2) Items of the data include INDEX, R-Time, AREA, HEIGHT, I-Time, F-Time, F-HEIGHT, MK, INDO, CONC, and NAME.
(3) A minimum value of HEIGHT is set at 150,000 as a quantitative parameter. A value of HEIGHT smaller than 150,000 is not necessary for determining the species.
(4) The data converted in the parameter setting is stored in a flexible disk or a storage medium.
(5) An analysis PC reads the stored data to create the database.

The database will be described in detail next.

(1) The database read by the analysis PC is individually controlled with Microsoft Office™ for each plant.
(2) Items of the database including the retention time, AREA, and HEIGHT, are controlled for measuring a flux quantity of a lignin component. Other items are not necessary for the species determination.

The digital conversion of the database will be described next.
(1) A flux quantity of a lignin component of each plant is output according to the retention time.
(2) A relationship between the flux quantity and the retention time is digitally converted to obtain a specific profile of the plant.
(3) The digital data is registered into a specific database to control the specific profile of the plant.

Accordingly, in the present invention, the time dependency of the flux quantity of the lignin component contained in the plant is digitally processed to a numerical value to create the database of the individual species, thereby determining the species rapidly and easily through the comparison between the measured result and the database.

Preferred embodiments of the present invention will be described next, and the invention is not limited to the embodiments.

First Embodiment

In the first embodiment, *Lolium multiflorum* Lam (Italian rye grass), *Lolium perenne* L. (perennial rygrass), *Dactylis glomerata* L. (orchard grass), *Panicum maximum* Jacq. (Guinea grass), *Chloris gayana* kunth (rose grass), *Trifolium pratense* L. (red clover), and *Trifolium repens* L. (white clover) supplied from the department of agriculture of the Miyazaki University, Japan, were analyzed.

A curie-point type thermal decomposition apparatus (GC-17A made by Shimazu Seisakusho) was used for the analysis under the following conditions.
  Column oven temperature: 50° C.
  Sample gasification chamber temperature: 170° C.
  Detecting apparatus temperature: 280° C.
  Column input pressure: 30 Kpa
  Gasification time: 70 minutes
  Samples were approximately 0.0014 g of dry stored ground samples obtained from whole portions of *Lolium multiflorum* Lam (Italian rye grass), *Lolium perenne* L. (perennial rygrass), *Dactylis glomerata* L. (orchard grass), *Panicum maximum* Jacq. (Guinea grass), *Chloris gayana* kunth (rose grass), *Trifolium pratense* L. (red clover), and *Trifolium repens* L. (white clover).

FIGS. 1(A) and 1(B) to 4(A) and 4(B) show analysis results of the dry stored ground samples of the respective species. As shown in FIGS. 1(A) and 1(B) to 4(A) and 4(B), the respective species have their own specific wave patterns of lignin, i.e., constitutes of cell walls. According to the first embodiment, the flux profiles or specific spectrums particular to the respective species are detected with sufficient repeatability to identify the species easily by comparing with the databases prepared in advance (for example, refer to FIGS. 8(A) and 8(B) to 12(A) and 12(B)).

Second Embodiment

In the second embodiment, dry tissue (leaf) samples of *Oryza sativa* L. (rice plant), *Imperata cylindrica* (L.) Beauv. (cogon grass), *Zoysia japonica* steud. (Japanese lawn grass), *Zoysia matrella* (L.) Merr. (malilagrass), *Zoysia tenuifolia* Willd. (Korean lawn grass), supplied from the department of agriculture of the Miyazaki University, Japan, were analyzed and detected in the same way as in the first embodiment. The detection results are shown in FIGS. 5(A) and 5(B) to 7. The digital databases of these species are shown in FIGS. 8(A) and 8(B) to 12(A) and 12(B).

The followings are known from the detection results.
(1) A mature leaf of the *Oryza sativa* L. has a peculiar spectrum.
(2) A mature leaf of the *Imperata cylindrica* (L.) Beauv. has a peculiar spectrum.
(3) A mature leaf of the *Zoysia japonica* steud. has a peculiar spectrum.
(4) A mature leaf of the *Zoysia matrella* (L.) Merr. has a peculiar spectrum.
(5) A mature leaf of the *Zoysia tenuifolia* Willd. has a peculiar spectrum.

According to the second embodiment, a flesh sample is not necessary for the analysis. That is, a characteristic spectrum particular to a species can be obtained from even an aged dry sample to easily determine the species in the same way as in the first embodiment.

Third Embodiment

In the third embodiment, dry stored ground samples of different tissues (a mature leaf and a stem) of *Chloris gayana* kunth supplied from the department of agriculture of the Miyazaki University, Japan, were analyzed and detected in the same way as in the first embodiment. The analysis results shown in FIGS. 13(A) and 13(B) for the leaf and the stem, respectively, indicate similar detection characteristics peculiar to the species. That is, both of the dry stored powder samples of the mature leaf and the stem of the *Chloris gayana* kunth have the spectrum patterns peculiar to the *Chloris gayana* kunth.

Figure 1A:
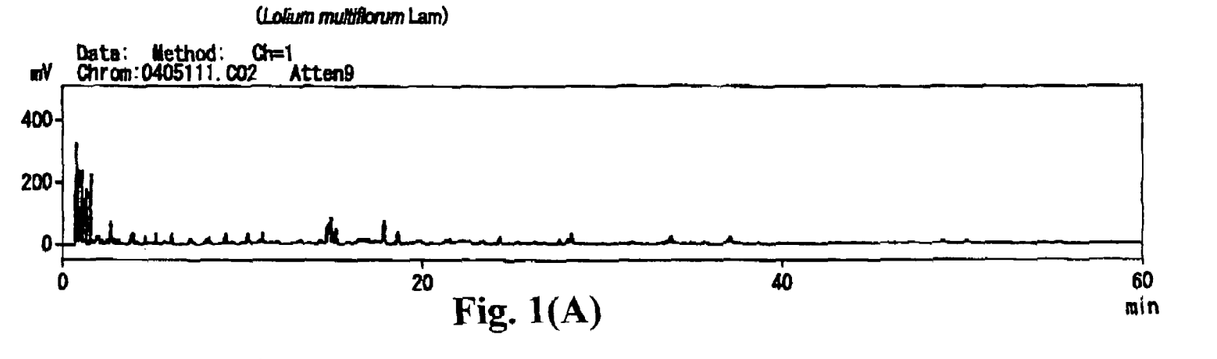
FIGS. 1(A) and 1(B) are spectrographs of dry ground samples of *Lolium multiflorum* Lam (Italian rye grass) and *Lolium perenne* L. (perennial rye grass), respectively.
Figure 1B:
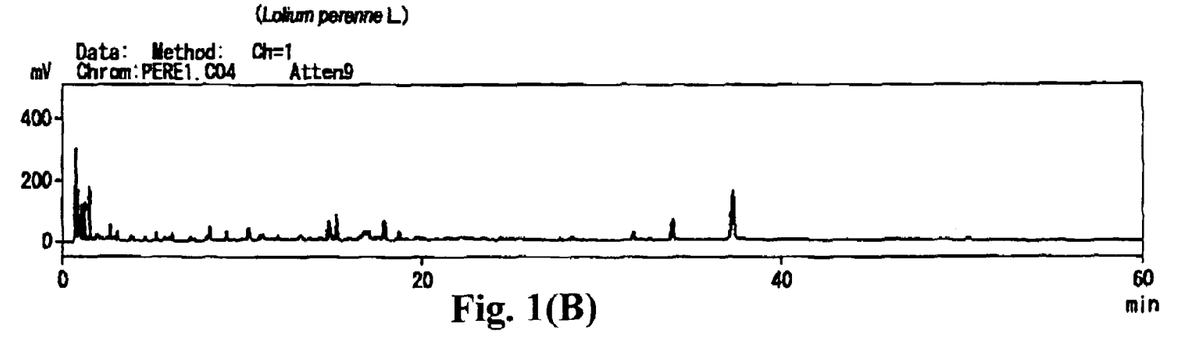
Figure 2A:
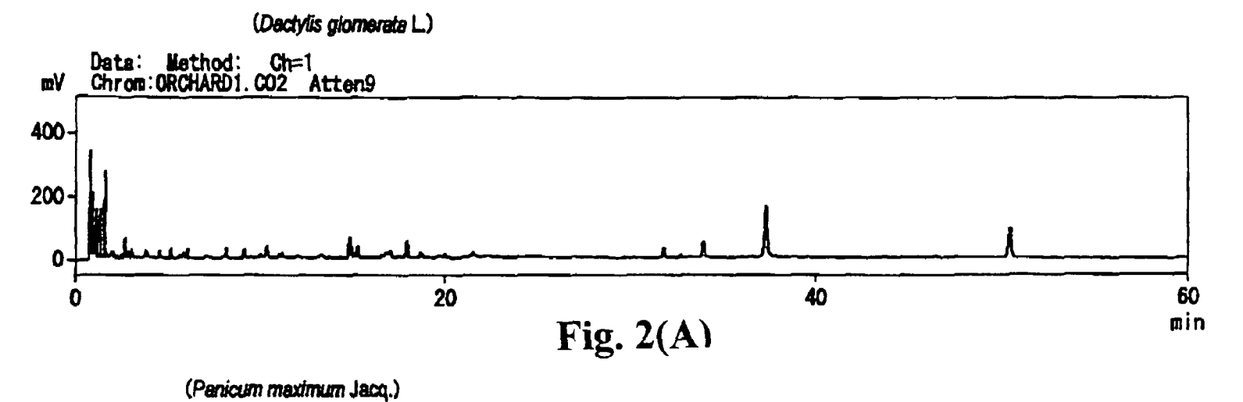
FIGS. 2(A) and 2(B) are spectrographs of dry ground samples of *Dactylis glomerata* L. (orchard grass) and *Panicum maximum* Jacq. (Guinea grass), respectively.
Figure 2B:
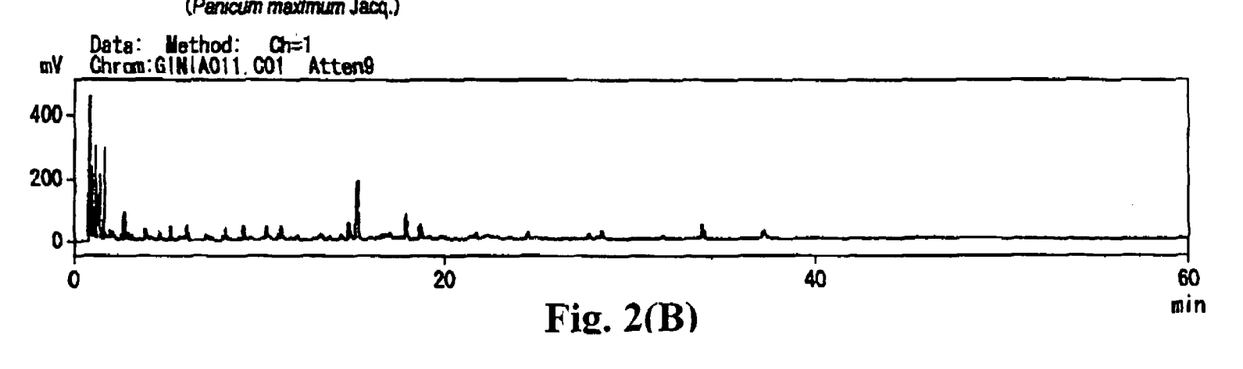
Figure 3A:
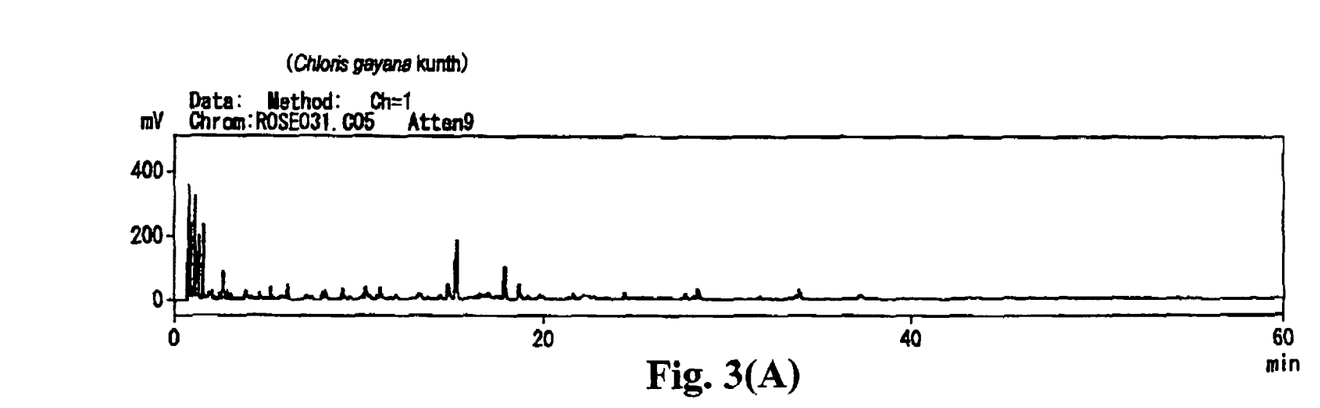
FIGS. 3(A) and 3(B) are spectrographs of dry ground samples of *Chloris gayana* kunth (rose grass) and *Trifolium pratense* L. (red clover), respectively.
Figure 3B:
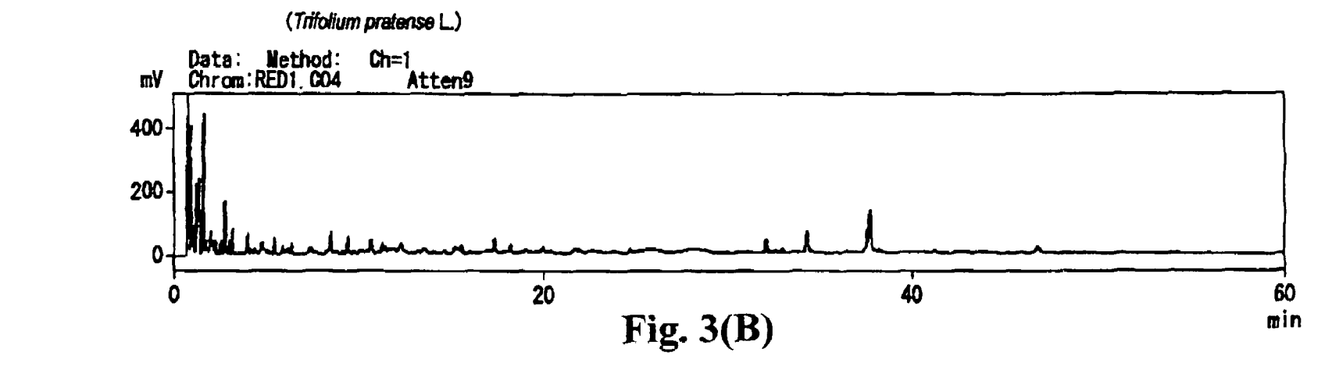
Figure 4:
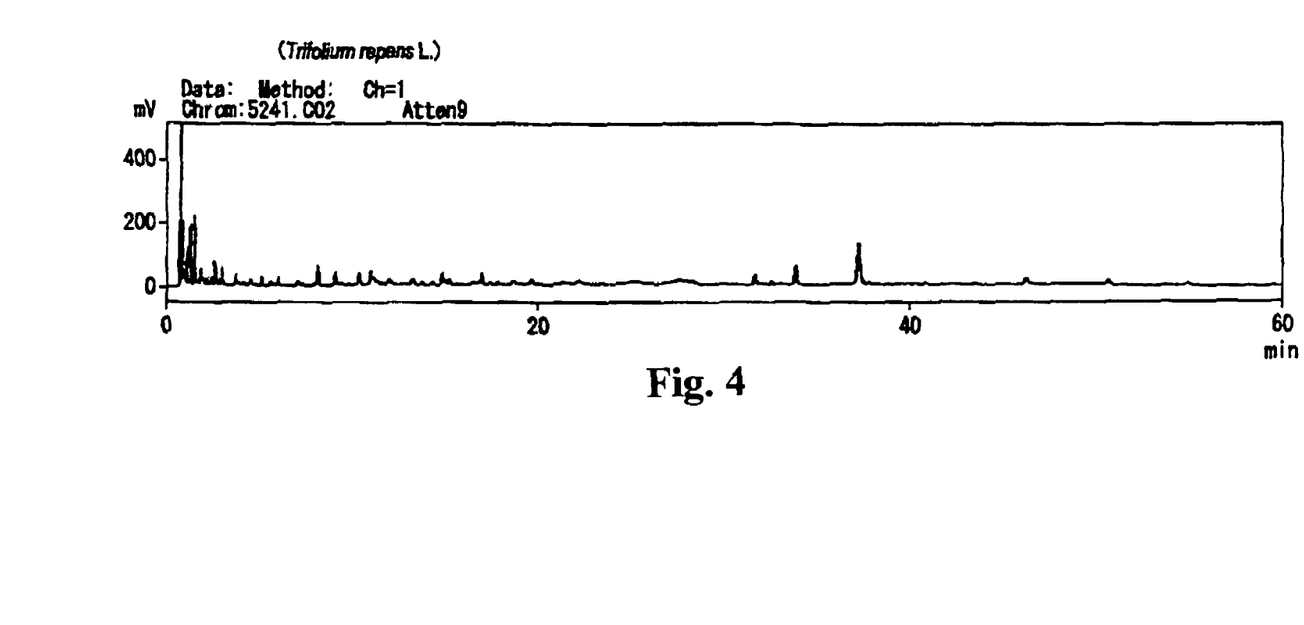
FIG. 4 is a spectrograph of a dry ground sample of *Trifolium repens* L. (white clover)
Figure 5A:
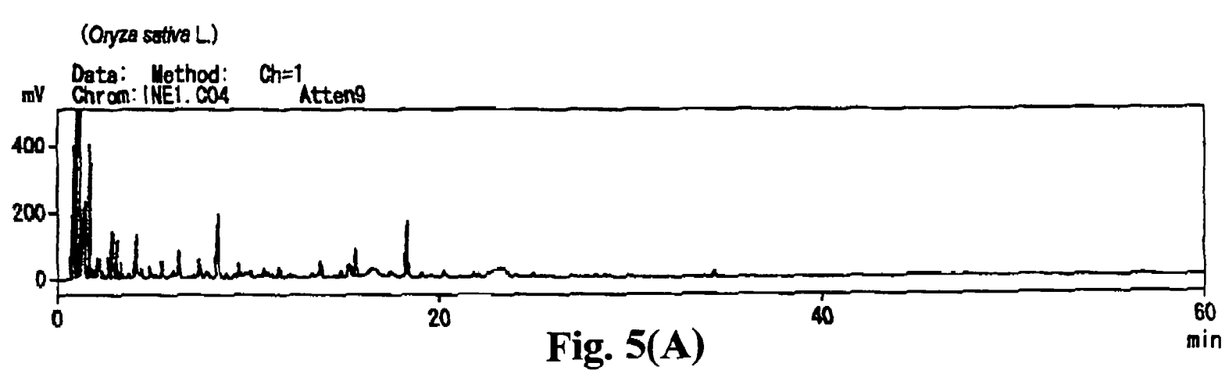
FIGS. 5(A) and 5(B) are spectrographs of dry tissues (leaves) of *Oryza sativa* L. (rice) and *Imperata cylindrica* (L.) Beauv. (cogon grass), respectively.
Figure 5B:
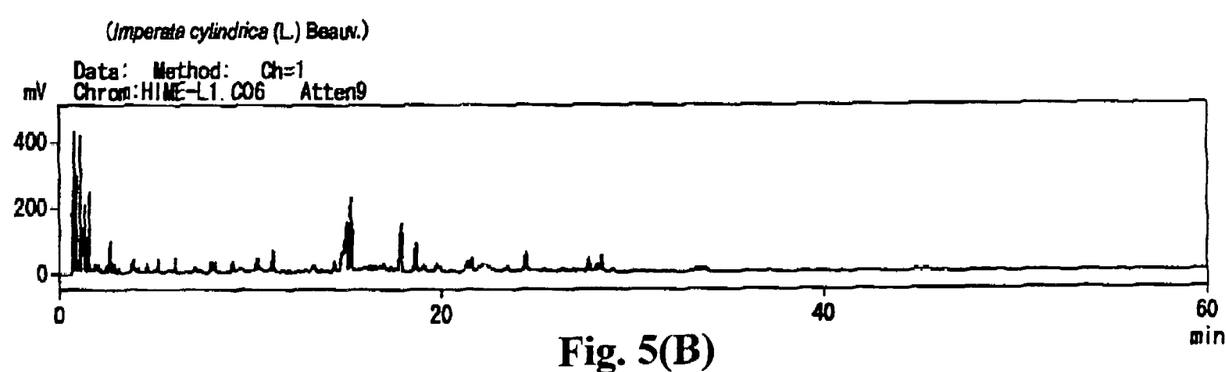
Figure 6A:
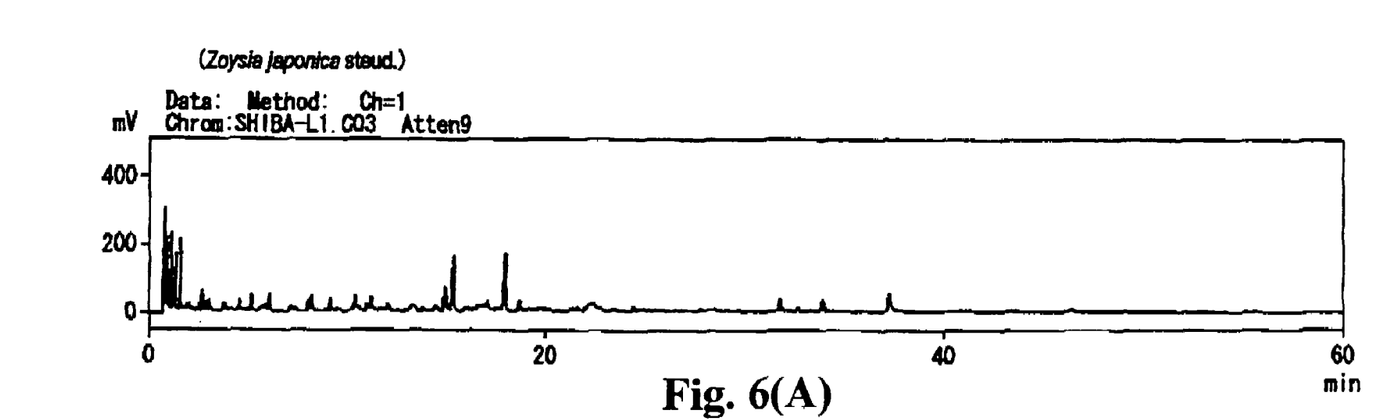
FIGS. 6(A) and 6(B) are spectrographs of dry tissues (leaves) of *Zoysia japonica* steud. (Japanese lawn grass) and *Zoysia matrella* (L.) Merr. (Malilagrass), respectively.
Figure 6B:
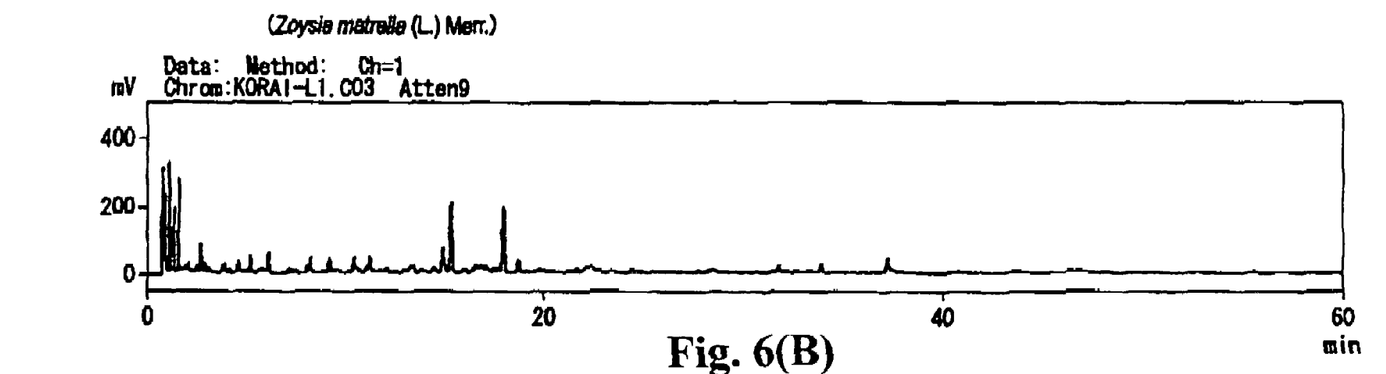
Figure 7:
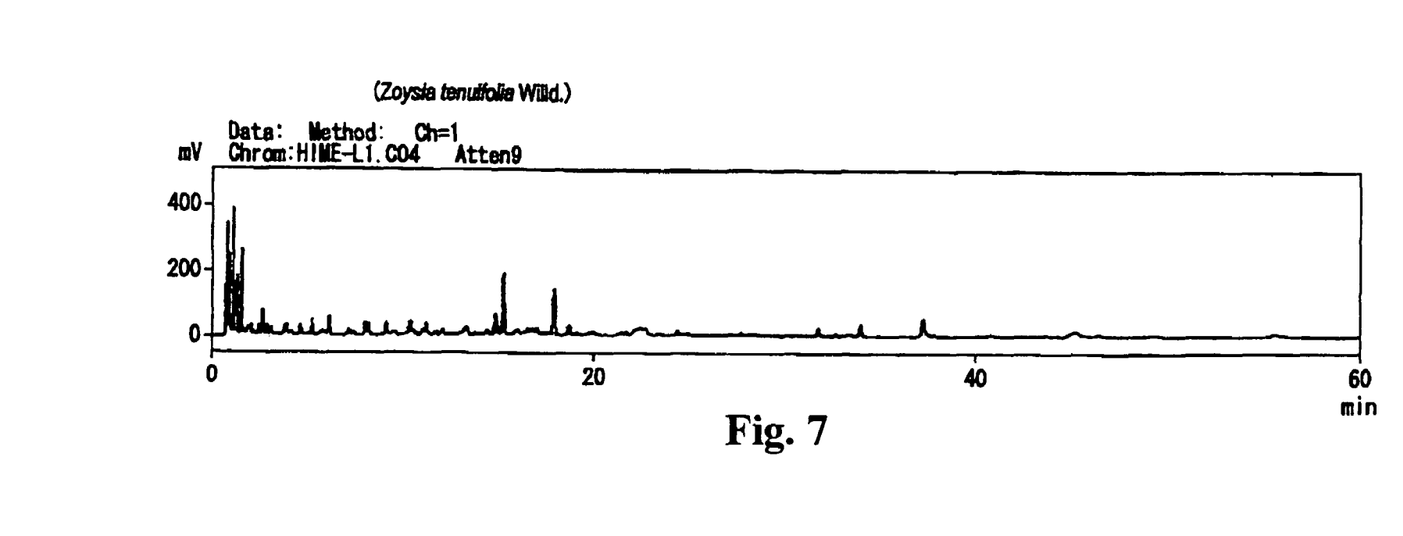
FIG. 7 is a spectrograph of a dry tissue (leaf) of *Zoysia tenuifolia* Willd. (Korean lawn grass)
Figure 8A:
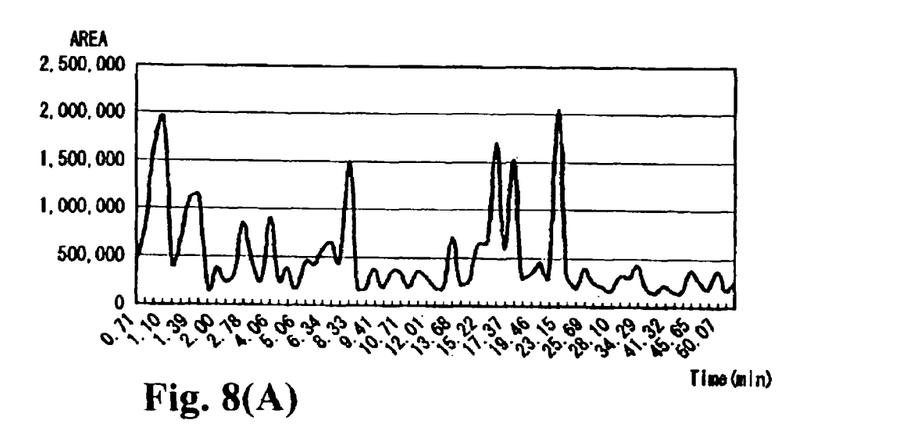
FIGS. 8(A) and 8(B) are views showing database of *Oryza sativa* L. (rice)
Figure 8B:
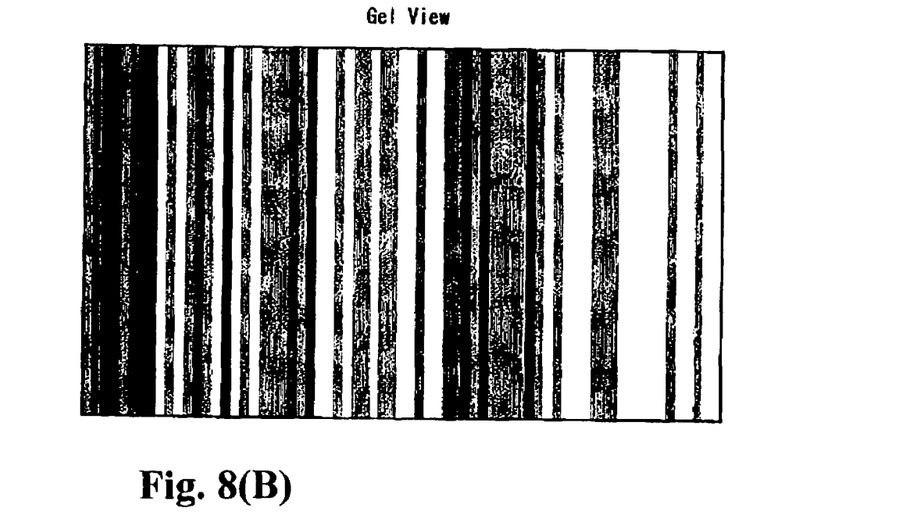
Figure 9A:
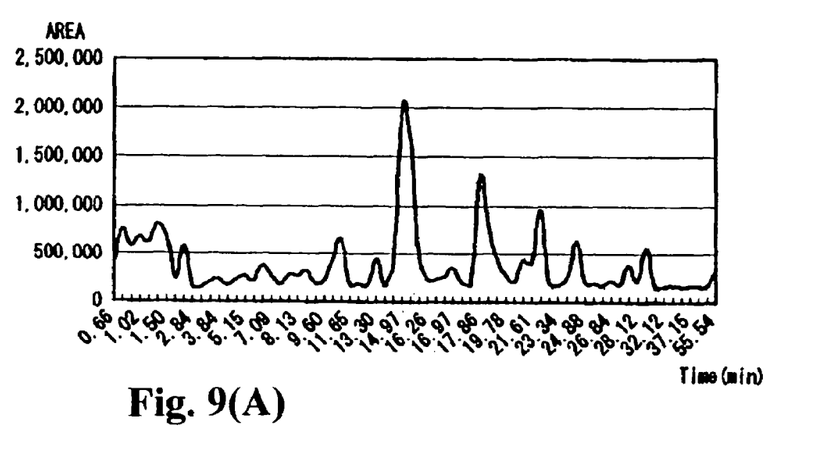
FIGS. 9(A) and 9(B) are views showing database of *Imperata cylindrica* (L.) Beauv. (cogon grass)
Figure 9B:
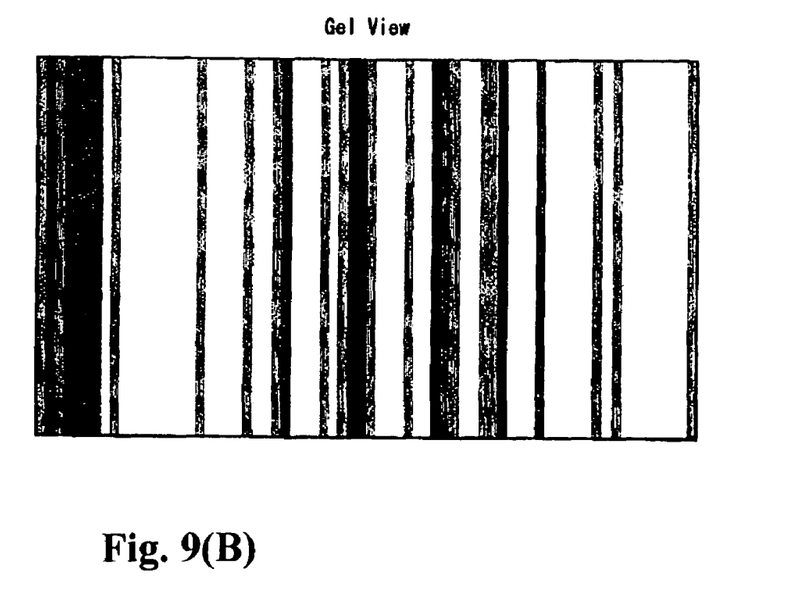
Figure 10A:
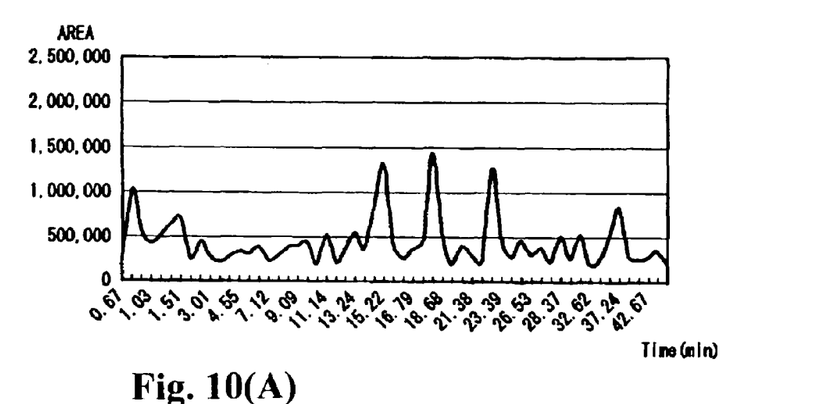
FIGS. 10(A) and 10(B) are views showing database of *Zoysia japonica* steud. (Japanese lawn grass)
Figure 10B:
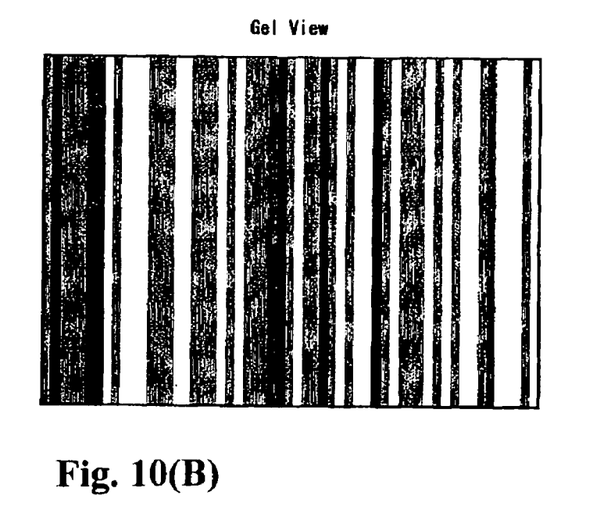
Figure 11A:
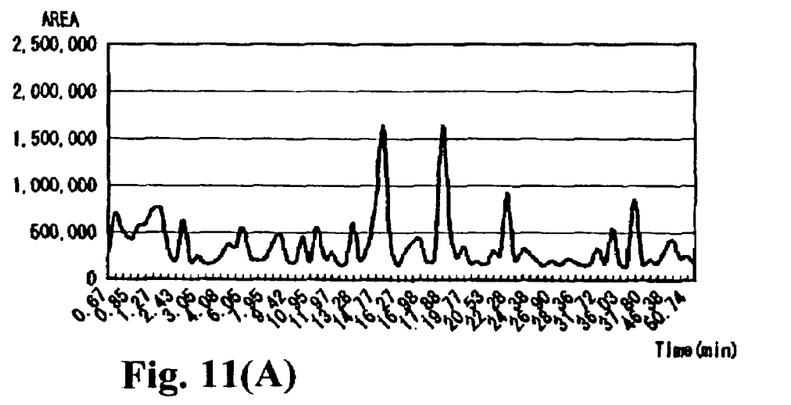
FIGS. 11(A) and 11(B) are views showing database of *Zoysia matrella* (L.) Merr. (Malilagrass)
Figure 11B:
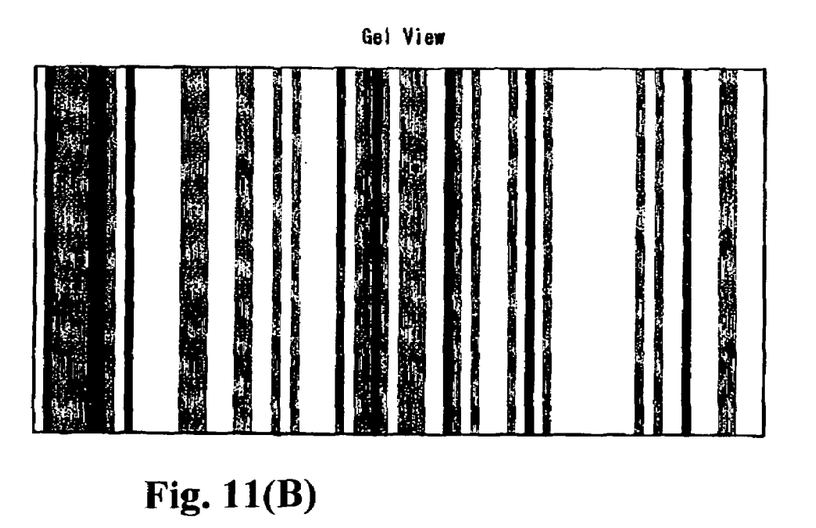
Figure 12A:
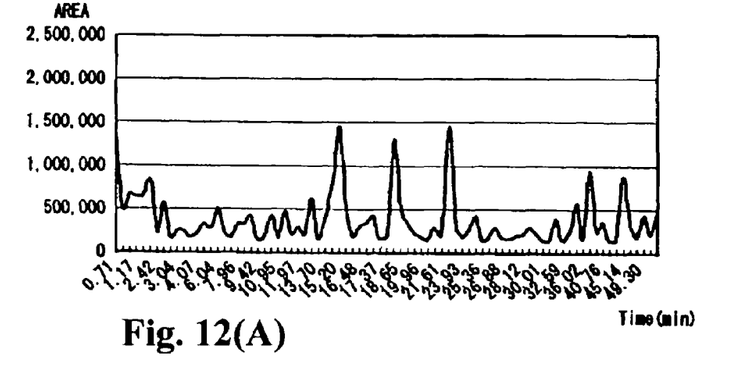
FIGS. 12(A) and 12(B) are views showing database of *Zoysia tenuifolia* Willd. (Korean lawn grass)
Figure 12B:
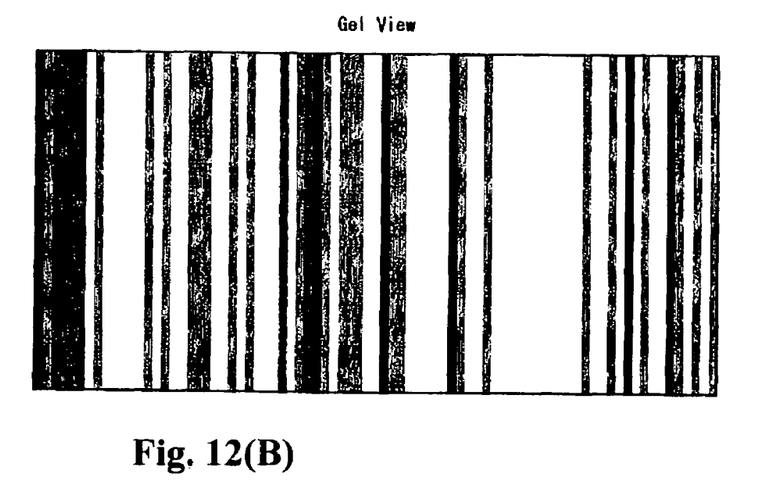
Figure 13A:
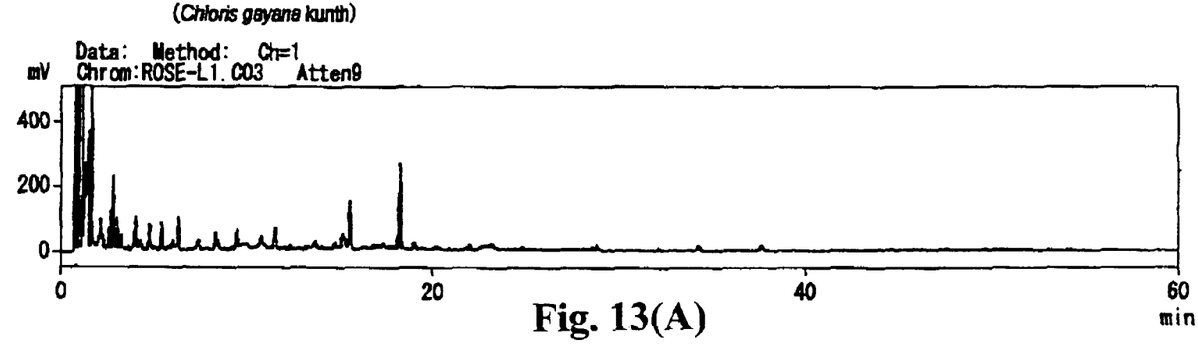
FIGS. 13(A) and 13(B) are spectrographs of dry ground samples of a leaf and a stem of *Chloris gayana* kunth (rose grass), respectively.
Figure 13B:
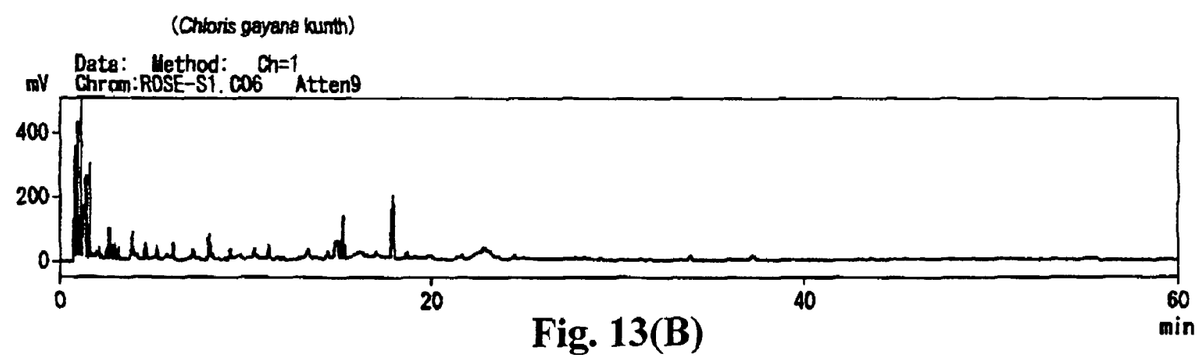

According to the third embodiment, even if the tissues are different, the detected spectrums are identical when the species of the tissues is identical. Therefore, the method of determining the species of the plant according to the invention is as reliable as the conventional method using a DNA. Moreover, the determination is performed very easily and rapidly at low cost.

When determining the species by the detected spectrum, even if there is difference in the value in the vertical axis of the spectrograph, a position of the peak of the value with respect to the retention time (horizontal axis) is almost identical, thereby making it possible to determine the species.

In the embodiments described above, the stored ground samples or the dried ground samples are used. In the present invention, the sample is used after being dried, so that a fresh sample may be used after the drying treatment. Further, it is possible to determine a species of a plant fragment discovered at an ancient ruin.

The disclosure of Japanese Patent Application No. 2004-307989, filed Oct. 22, 2004, is incorporated in the application.

While the invention has been explained with reference to the specific embodiments of the invention, the explanation is illustrative and the invention is limited only by the appended claims.

What is claimed is:
1. A method of identifying a plant species, comprising the steps of:
  gasifying a plurality of reference plant samples over a specific period of time to obtain lignins of the reference plant samples;
  obtaining reference flux profiles of the lignins of the reference plant samples with pyrolysis-gas chromatography;
  creating a data base correlating the reference plant samples to the reference flux profiles;
  preparing a fragment of a plant specimen;
  gasifying the fragment at a high temperature to obtain a lignin of the fragment over a specific period of time;

obtaining a flux profile of the lignin with pyrolysis-gas chromatography; and comparing the flux profile to the reference flux profiles in the data base to determine the species of the plant specimen.

2. The method of identifying a plant species according to claim 1, wherein, in the step of preparing the fragment, said fragment is obtained from a tissue of the plant specimen.

3. The method of identifying a plant species according to claim 1, wherein said fragment includes powder or has a size of 2-3 mm.

4. The method of identifying a plant species according to claim 1, wherein, in the step of obtaining the flux profile, said flux profile includes time-based spectrum data of flux quantities of the lignin.

5. The method of identifying a plant species according to claim 1, wherein, in the step of comparing the flux profile, said flux profile is digitally processed before being compared with the database.

6. The method of identifying a plant species according to claim 1, wherein, in the step of gasifying the fragment, said gasification is performed at a temperature of 150° C. to 190° C.

7. The method of identifying a plant species according to claim 1, wherein, in the step of preparing a fragment of a plant specimen, said plant specimen is dried until moisture content thereof becomes 10% or less.

8. The method of identifying a plant species according to claim 1, wherein, in the step of preparing a fragment of a plant specimen, said fragment has a weight of 10 to 100 mg.

9. The method of identifying a plant species according to claim 2, wherein said tissue includes a leaf, a stem, or a root.

10. The method of identifying a plant species according to claim 1, wherein, in the step of preparing a fragment of a plant specimen, said fragment is spread to form a thin film.

* * * * *